US00PP22395P2

(12) United States Plant Patent
Egger

(10) Patent No.: US PP22,395 P2
(45) Date of Patent: Dec. 20, 2011

(54) ***HEUCHERELLA* PLANT NAMED 'GUNSMOKE'**

(50) Latin Name: ***Heucherella* hybrid**
Varietal Denomination: Gunsmoke

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/806,923

(22) Filed: Aug. 23, 2010

(51) Int. Cl.
*A01H 5/00* (2006.01)

(52) U.S. Cl. ..... Plt./441

(58) Field of Classification Search ..... Plt./441
See application file for complete search history.

*Primary Examiner* — Annette Para
(74) *Attorney, Agent, or Firm* — Klarquist Sparkman, LLP

(57) ABSTRACT

A new and distinct *Heucherella* plant substantially as shown and described, characterized by large, rose plum to silver palmatifid leaves, prominent dark veins in summer through winter leaves, a large mounding plant habit, grows equally well in full sun or filtered shade in the Pacific Northwest, and excellent vigor.

1 Drawing Sheet

Botanical denomination: *Heucherella* hybrid.
Variety designation: 'Gunsmoke'.

The present invention relates to a new and distinct cultivar of *Heucherella* and given the cultivar name of 'Gunsmoke'. *Heucherella* is in the family Saxifragaceae. *Heucherella* 'Gunsmoke' originated from a controlled cross between *Heuchera* 1053-1 (a proprietary unreleased *Heuchera villosa* hybrid), as the seed parent, and massed selected proprietary *Tiarella*, as the pollen parent.

Compared to the seed parent *Heuchera* 1053-1, the new variety has leaves that are palmatifid rather than palmately lobed.

There are no *Heucherella* on the market that are similar.

This new *Heucherella* is distinguished by:

1. large, rose plum to silver palmatifid leaves,
2. prominent dark veins in summer through winter leaves
3. a large mounding plant habit,
4. grows equally well in full sun or filtered shade in the Pacific Northwest,
5. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one and a half year old *Heucherella* 'Gunsmoke' in bloom in May, growing in the ground in full sun in the garden in Canby, Oreg.

FIG. 2 shows the foliage color of a one and a half year old *Heucherella* 'Gunsmoke' late summer in Canby, Oreg.

DETAILED PLANT DESCRIPTION

The following is a detailed description of the new *Heucherella* cultivar based on observations of a two-year-old specimens growing in the ground in the garden in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—33 cm tall from top of the foliage to the ground and 64 cm wide.
*Habit.*—Mounding.
*Vigor.*—Excellent.
*Roots.*—Fibrous, freely branching, fine, and white in color.

Leaf:

*Type.*—Simple.
*Arrangement.*—Rosette.
*Shape.*—Ovate to orbicular.
*Lobing/division.*—Palmatifid with 5 lobes, the terminal the longest, each with shallow secondary lobes.
*Venation.*—Palmate.
*Margins.*—Crenate.
*Apex.*—Mucronulate.
*Base.*—Cordate, sometimes overlapping.
*Blade size.*—Grows to 19 cm long and 18 cm wide, usually smaller.
*Surface texture.*—Both surfaces glandular.
*Petiole description.*—Grows to 25 cm long and 3.5 mm wide, glandular hairs, Greyed Orange 177A.
*Leaf color.*—Spring topside, closest to Greyed Purple N186C with a silver pink interveinal veil, between Red Purple 69C and Greyed Purple N187C, bottom side Greyed Purple 187B; summer topside, veins Greyed Purple 187A to N186A with silver veil closest to Greyed Purple N187D, bottom side between Greyed Purple N186C and Greyed Purple N187C.

Inflorescence:

*Size.*—3 cm wide and 15 cm long.
*Type.*—Raceme.
*Number of flowers per raceme.*—About 30.
*Number of racemes.*—About 10.

*Peduncle.*—Grows to 38 cm tall, 3 mm wide at base, Greyed Orange 177A, glandular hairs, no cauline leaves.

*Pedicel.*—Grows to 4 mm long, with glandular hairs, Greyed Purple 187A.

*Bloom period.*—May to July in Canby, Oreg.

Flower bud:

*Size.*—1.5 mm wide and 2.7 mm long.

*Description.*—Glandular puberulent, ovoid.

*Color.*—Bottom ⅓ Red Purple 69A, top ⅔ White NN155C.

Flower:

*Type.*—Perfect.

*Shape.*—Campanulate.

*Size.*—5 mm deep and 6 mm wide.

*Petal description.*—5 in number, oblanceolate, 4 mm long and 1 mm wide, tip acuminate, base attenuate, margin entire, glabrous on both sides, White NN155D on both sides.

*Calyx description.*—3 mm deep and 4 mm wide, with 5 lobes, divided ½ way to the base, campanulate, glandular hairs on outside, glabrous inside, tip obtuse, margin entire, White NN155C on both sides with tips Yellow Green 146A and outside base Red Purple 69D.

*Stamen description.*—10 in number, filaments 3 mm long, White NN155D, anthers sterile, less than 1 mm, White 155C.

*Pistil description.*—One central two beaked pistil, 5 mm long, White NN155C.

*Fragrance.*—None.

*Lastingness.*—Each raceme blooms for about 2 weeks on the plant.

Fruit and seed: None

Disease and pest tolerance: No known resistances. Excellent disease tolerance to powdery mildew. All *Heucherella* are susceptible to root weevils.

I claim:

1. A new and distinct *Heucherella* plant as herein illustrated and described.

* * * * *

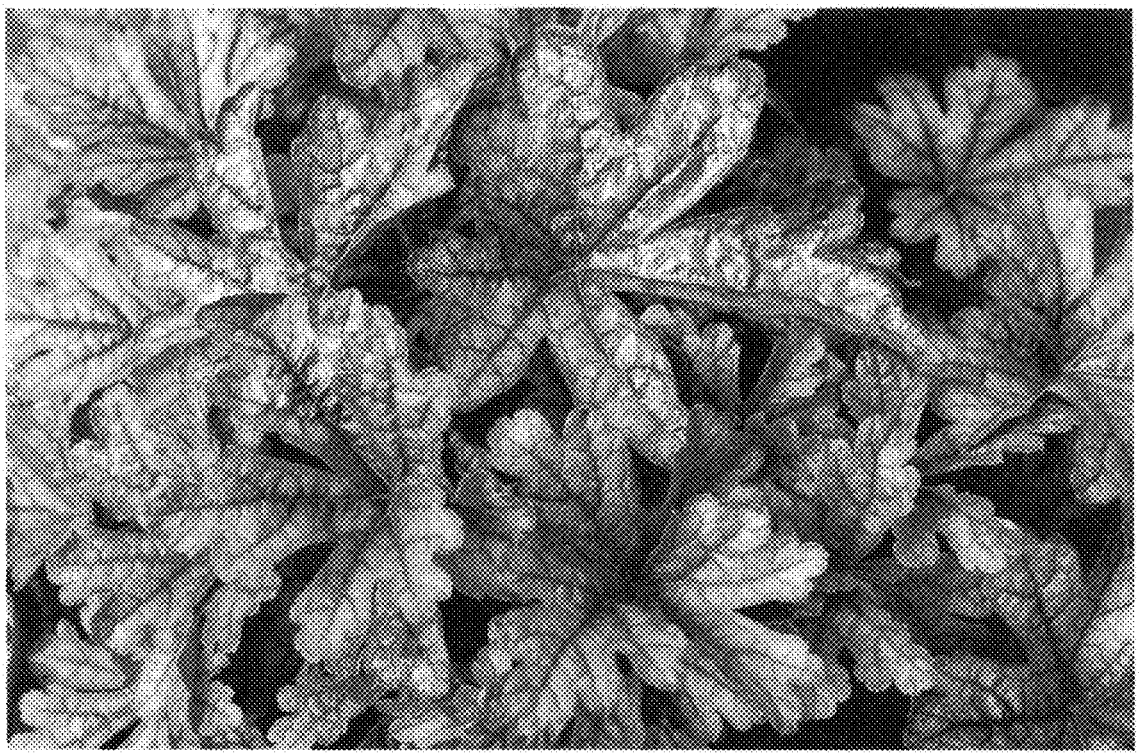

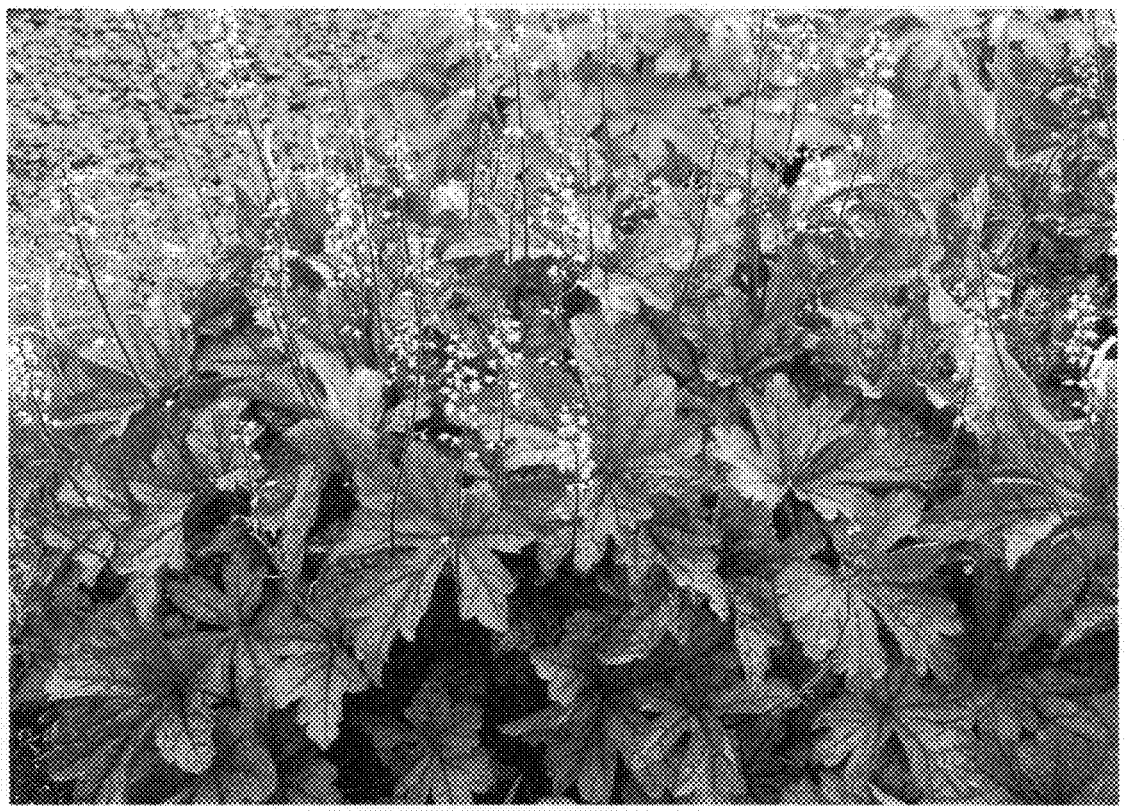
Figure 1 above. Figure 2 below.